United States Patent [19]

Fragnet

[11] 4,226,246
[45] Oct. 7, 1980

[54] APPARATUS FOR MAINTAINING THE NEGATIVE POTENTIAL OF HUMAN, ANIMAL, AND PLANT CELLS

[75] Inventor: Jean Fragnet, Susy-en-Brie, France

[73] Assignee: Carba Societe Anonyme, Switzerland

[21] Appl. No.: 908,638

[22] Filed: May 23, 1978

[30] Foreign Application Priority Data

May 27, 1977 [CH] Switzerland .......................... 6578/77

[51] Int. Cl.³ ............................................. A61N 1/36
[52] U.S. Cl. ................................................ 128/420 R
[58] Field of Search ........... 128/419 R, 419 F, 420 R, 128/420 A, 421–422, 404–405, 423

[56] References Cited

U.S. PATENT DOCUMENTS

| | | | |
|---|---|---|---|
| 3,096,768 | 7/1963 | Griffith, Jr. | 128/420 A |
| 3,835,833 | 9/1974 | Limoge | 128/420 R |
| 3,885,573 | 5/1975 | Hara | 128/420 |
| 3,908,669 | 9/1975 | Man et al. | 128/422 |
| 3,955,583 | 5/1976 | Hörauf | 128/420 R |
| 3,978,864 | 9/1976 | Smith et al. | 128/404 |
| 4,119,102 | 10/1978 | LeVeen | 128/422 |
| 4,124,030 | 11/1978 | Roberts | 128/422 |

OTHER PUBLICATIONS

Fridlund, A. J. et al., "An Inexpensive IC Intracranial Stimulator", Behav. Res. Meth. & Instr., vol. 8, No. 1, pp. 21-23, Feb. 1976.

Dascalov, I. C., "Digital Electrostimulator" Med. & Biol Engr., Jan. 1974, vol. 12, No. 1, pp. 137–138.

Primary Examiner—Robert W. Michell
Assistant Examiner—Francis J. Jaworski
Attorney, Agent, or Firm—Roylance, Abrams, Berdo & Farley

[57] ABSTRACT

The disclosed apparatus includes a generator which is controllable by means of a control circuit and produces high frequency pulses of adjustable repetition frequency and duration. It also includes a circuit which produces a d.c. voltage and a pulsating d.c. voltage for ionization, as well as pulses of specific shape and variable repetition frequency for the faradization of the tissue to be treated. A treatment head features a disk-like insulating plate which is metal-coated on one side in an annular pattern and on the other side in a spiral pattern. Various specific circuit elements and blocks are described. The type of apparatus involved is intended for use in therapy, among other possible applications.

3 Claims, 10 Drawing Figures

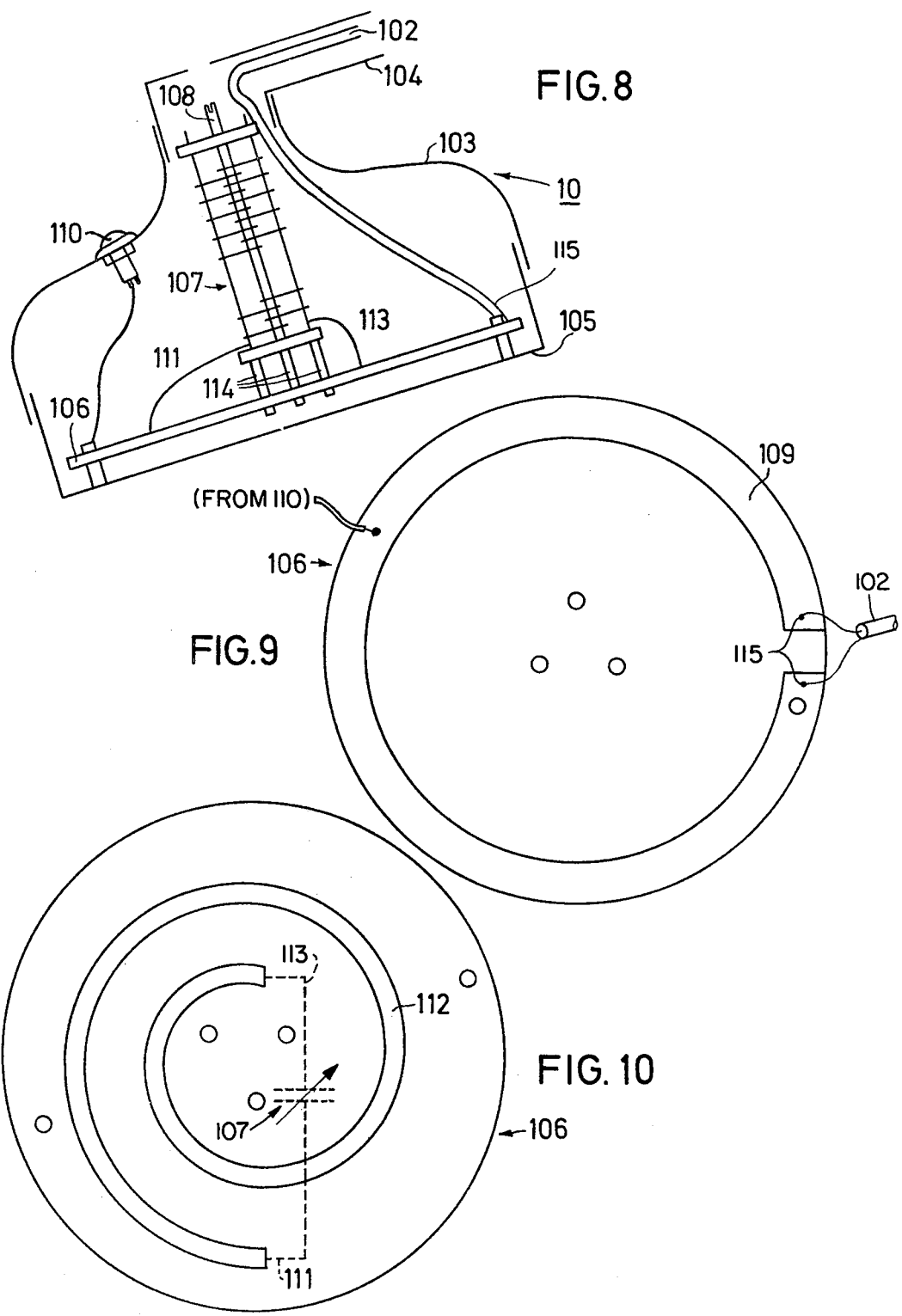

4,226,246

APPARATUS FOR MAINTAINING THE NEGATIVE POTENTIAL OF HUMAN, ANIMAL, AND PLANT CELLS

BACKGROUND OF THE INVENTION

The invention relates to an apparatus for maintaining the negative potential of human, animal and vegetable cells and/or for the penetration of substances into the cells.

It has been found that when electromagnetic fields are applied to the cells of human, animal or vegetable tissues, the cells become oriented in the direction of the field. Depending on the type of tissue, either the cell itself or only the molecules within the cell undergo this rotation. In the case of a continuously supplied field, all the cells remain polarized, so that current can flow through the cells. When pulses are used, i.e. in the case of an intermittent supply of energy to the cells, the latter attempt to rotate in the direction of the electromagnetic field. Following the pulse, the cells rotate back into their original position. If the pulse is long, the cells remain polarized too long, whereas in the case of a short pulse the cells have no time to rotate. The interval between the individual pulses must be made sufficiently long for the cells to have adequate time therein to rotate back into the original position. Thus, the principle also applies here that no action can be exerted by the too long or the too short intervals between the individual pulses. The microscopic displacement of the cell caused by the influence of the electromagnetic field results in a so-called micro-trauma on the surrounding tissue. The human, animal or vegetable tissue behaves in the same way as matter having a crystalline structure. Thus, the tissue is able to convert a mechanical energy into an electromagnetic energy and vice versa (piezoelectric effect). A mechanical pressure exerted on a piezoelectric, crystalline structure produces a current which mobilizes the negative electrons. In the same or a similar manner, the application of an intermittent electromagnetic field to the cells or to a tissue of a human, animal or vegetable nature causes a mobilization of the negatively charged electrons.

SUMMARY OF THE INVENTION

In accordance with the present invention, a generator which can be controlled by a control circuit generates high frequency pulses of adjustable repetition frequency and duration and a circuit produces a d.c. voltage and a pulsating d.c. voltage for the ionization and pulses of specific shape and variable repetition frequency for the faradization of the tissue to be treated. This permits the negative potential in human, animal or vegetable cells to be maintained and additionally the transport of substances to cells and the penetration of the cells by them.

BRIEF DESCRIPTION OF THE DRAWINGS

The invention will be described in greater detail hereinafter relative to preferred embodiments and with reference to the attached drawings, which show:

FIG. 8 a side sectional view of a high frequency treatment head for the apparatus of FIG. 1.

FIG. 9 an end view of a plate of the head of FIG. 8.

FIG. 10 an end view of the other side of the plate of FIG. 8.

DETAILED DESCRIPTION OF THE PREFERRED EMBODIMENTS

Figure 1:
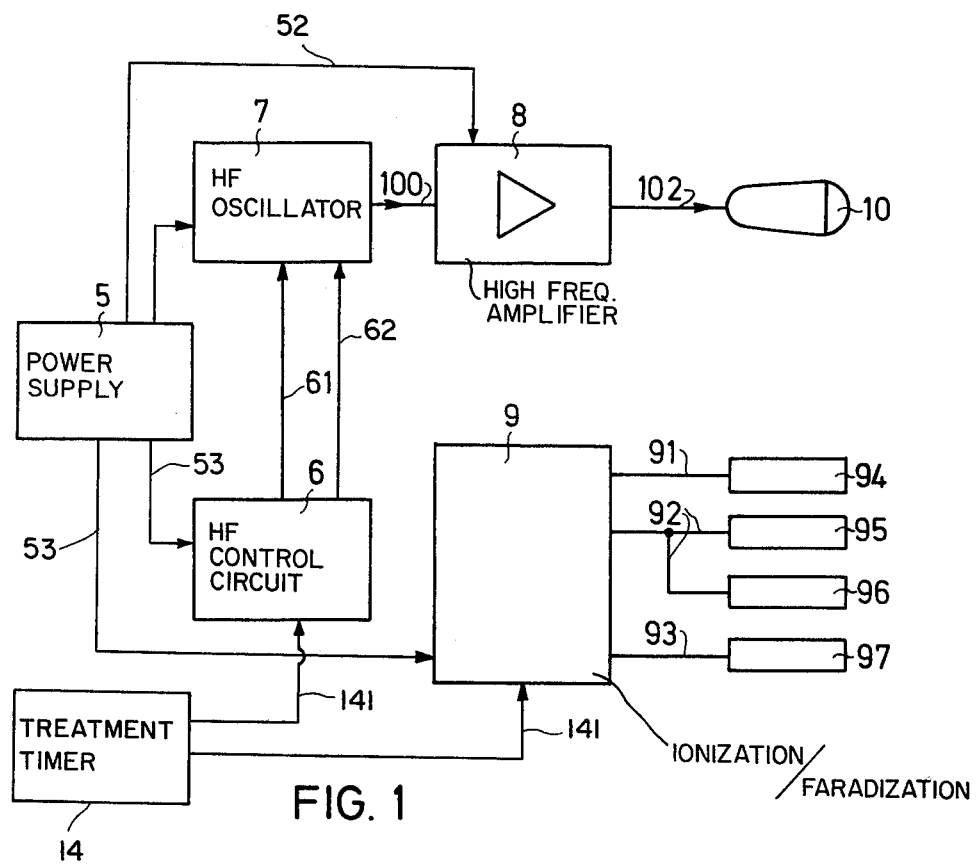
FIG. 1 a block diagram of a complete apparatus in accordance with a preferred embodiment of the present invention.

A preferred embodiment of the present invention is shown in FIG. 1 and comprises power supply means 5, comprising normal known components such as a transformer, rectifier circuit and voltage dividers. Power supply means 5 generates two voltages, specifically 24 V on conductor 53 for the complete control system of the apparatus and 60 V on conductor 52 for the high frequency final amplifier 8. There is derived from the 24 volts supplied by the power supply on lead 53 all of the lower voltages such as the 12 volts supplied by the regulator of FIG. 4 on lead 62 for use by the control circuits of FIG. 4 and various solid state circuits referred to elsewhere. The high frequency oscillator 7, described in greater detail relative to FIG. 5, comprises the oscillator part and the preamplifier part and generates a high frequency of e.g. 27.12 MHz. Control circuit 6 gives the oscillator 7 control commands via path 61 for the amplitude, the repetition frequency and the duration of the scanned high frequency of high frequency pulses. The composite wave form shown at the junction of the two capacitors coupling T 10 and T 11 of FIG. 5 contains, within the envelope formed by the repetition rate oscillator of FIG. 4 on line 61, the high frequency oscillations of oscillator T-9 of FIG. 5. These high frequency pulses of adjustable repetition frequency and adjustable duration reach high frequency final amplifier 8, via path 100, where the voltage is amplified to approximately 300 V. The thus amplified high frequency pulses pass to the antenna, or treatment head 10 via path 102 which is moved closer to the tissue to be treated. To a certain extent, control circuit 6 also controls circuit 9, which via leads 91 and 92 provides the steady or pulsating d.c. voltage for ionization and via leads 92 and 93 provides the d.c. voltage pulses of desired shape and repetition for faradization. The corresponding electrodes 94, 95 (ionization) and 96, 97 (faradization) are placed on the tissue to be treated. At this point, it is pointed out that the penetration of substances, such as e.g. medicaments into the tissue to be treated and which take place through the action of electrode 94, 95, is intensified and improved if the high frequency treatment head 10 is moved up to that same piece of tissue. The intermittent electromagnetic field applied by treatment head 10 leads to the ion transport brought about by the two ionization electrodes 94, 95 encountering a reduced resistance in the tissue. The moving closer of the antenna or the treatment head 10 also leads to an improvement to the faradization, brought about by the two other electrodes 96, 97. Pulsating d.c. voltage is employed where nerves, muscles or tendons are to be stimulated. Heretofore, the disadvantage has been that stimulation has only been performed to an inadequate extent. The application of the intermittent electromagnetic field through the treatment head 10, in addition to the pulsating d.c. voltage of electrodes 96, 97 provides the advantage that the treated tissue demonstrates much better electrolytic properties. It is pointed out that tissue relates to nerve, muscle and tendon tissue. As the intermittent electromagnetic field has a specific repetition frequency and a specific pulse duty factor, which will be explained in greater detail hereinafter relative to the other drawings, there is no heating of the treated tissue and metal parts, such as e.g. the applied electrodes 94, 95, 96, 97. Thus, it is possible with the treatment head or antenna 10 to supply a power which is adapted in optimum manner to the tissue. There is no need to take precautions regarding the electrodes. Thus, the pulse repetition frequency, duty factor, and duration can easily and effortlessly be independently and asynchronously adjusted for the high frequency, ionization and faradization modes of operation so as to be adapted to the various types of tissue. With the heretofore known apparatus, it was not possible to simultaneously apply high frequency therapy as well as ionization and faradization.

Figure 2:
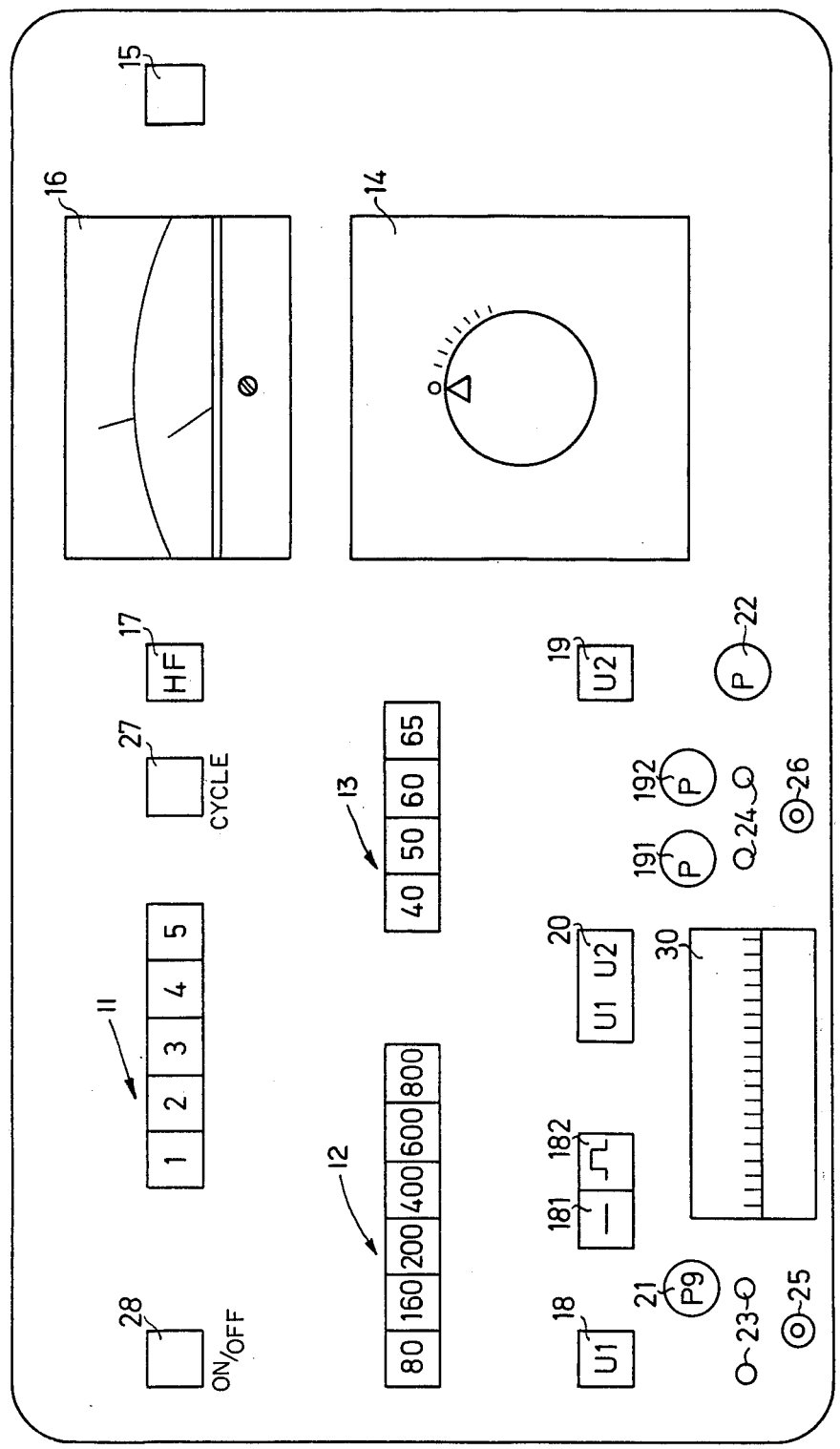
FIG. 2 a front panel of the apparatus of FIG. 1 with all the adjusting controls.

The various possible settings of the invention will now be explained relative to FIG. 2. FIG. 2 shows the front of the apparatus with all the setting devices. Keyboard 11 comprises five automatic contacts which can be activated one at a time, and, which can either be in the form of push buttons or contact buttons. These buttons are used to set the desired energy stage or level. Thus, for example, button 1 can be used for setting the lowest energy stage and button 5 the highest energy stage of high frequency pulses produced by generator 7. These buttons directly operate the control circuit 6. Keyboard 12, which is also directly connected to control circuit 6, selects the desired pulse repetition frequency. FIG. 2 shows six buttons, which can be in the form of contact or push buttons covering a range of 80 to 800 Hz. The buttons of keyboard 12 can also cover a range of 10 to 1000 Hz. The duration or time interval for each high frequency pulse is determined by keyboard 13, which is also directly connected with control circuit 6. FIG. 2 shows four buttons covering a range of 40 to 65 μsec, but a larger range of 10 to 100 μsec is also possible. On depressing the desired button in keyboards 11, 12 and 13, the desired time of high frequency application to the tissue is set by means of clock or timer 14. At the end of the desired treatment time, i.e. when the hand is in the zero position shown in FIG. 2, the control circuit 6 is switched off, so that treatment is at an end. As in practice several apparatuses are in operation at once and are supervised by only one person, there is provided an optical or acoustic indicating instrument 15, which announces or indicates the end of treatment. Furthermore, an indicator 16 is provided which indicates the energy supplied and the pulse repetition frequency. It can be an analogue or digital indicator 16. A further device 17, which can be in the form of a lamp, lights up when the high frequency final amplifier 8 is in operation. If final amplifier 8 fails, this lamp is extinguished.

If a d.c. voltage is to be used for ionization via electrodes 95 and 94 of FIG. 1, button 18 is depressed. If a continuous direct current is to be used for ionization, button 181 is additionally depressed. If a pulsating direct current is to be used for the ionization, button 182 is additionally depressed buttons 181 and 182 being interlocked so that only one can be depressed at a time.

Figure 7:
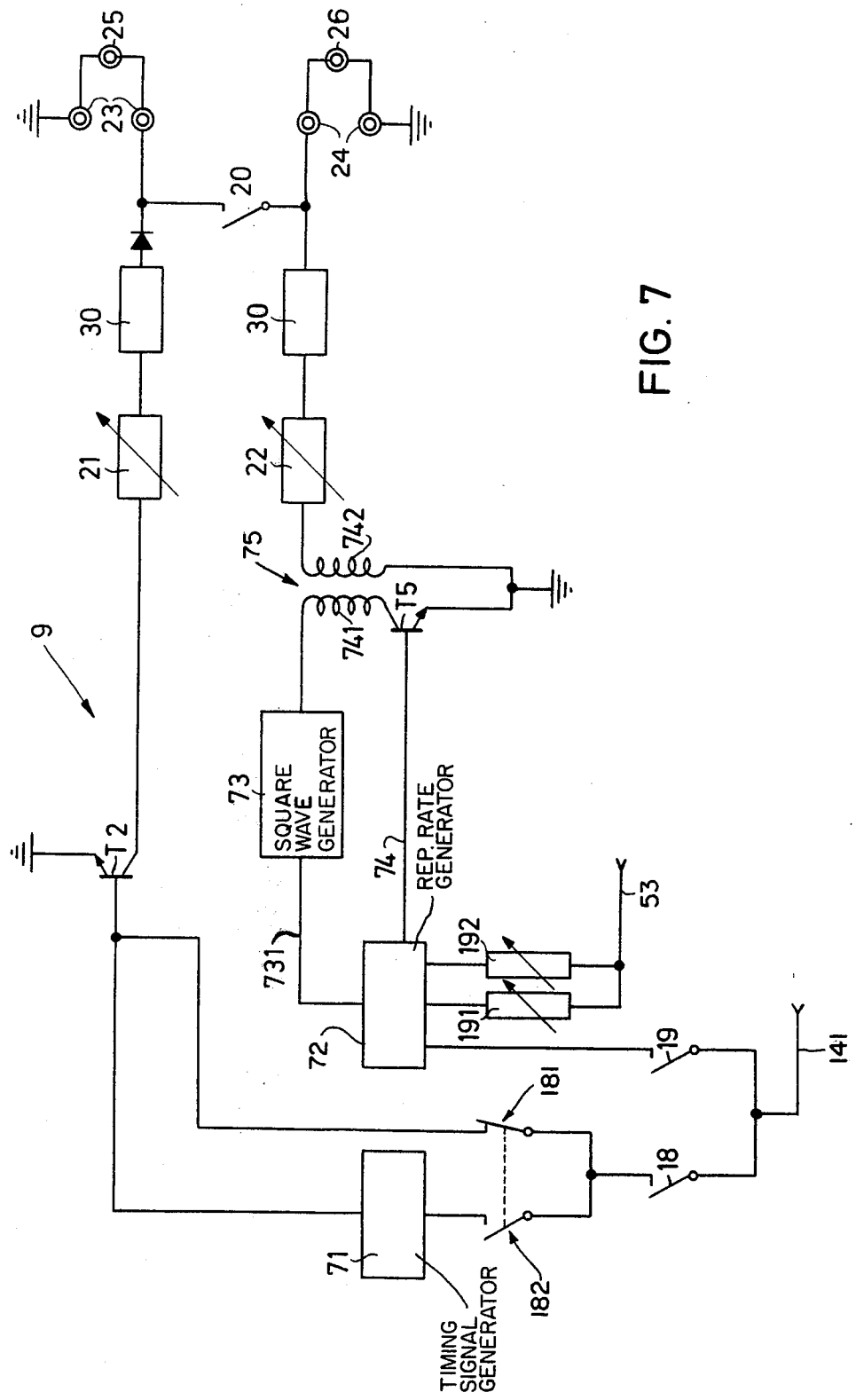
FIG. 7 an apparatus for ionization and/or faradization.

If the tissue is to be treated by faradization via electrodes 96 and 97, button 19 according to FIG. 2 is depressed. In the case of faradization treatment, pulses of specific shape and variable repetition frequency are applied to the tissue under treatment. The shape of the pulses can be trapezoidal, triangular, sinusoidal, saw-tooth shaped or the like. In the present case, the pulses have, for example, a saw-tooth shape. In the case of faradization, potentiometer 191 is used to set the length of the saw-tooth voltage pulses. Potentiometer 192 sets the desired repetition frequency of the faradization pulses. If both ionization and faradization are to be used for the tissue, then button 20 is depressed along with 18 and 19 according to FIG. 2. On setting the desired treatment procedure by operating the corresponding buttons, clock 14 is set to the desired treatment period. When the hand of clock 14 has returned to zero, ionization and/or faradization is stopped. It is pointed out here that clock 14 is used for high frequency treatment, ionization, and faradization. FIG. 2 also shows the two knobs 21, 22, whereby knob 21 operates a potentiometer in circuit 9 which adjusts the intensity of the current flowing between electrodes 94 and 95, while knob 22 moves a potentiometer located in circuit 9 for adjusting the saw-tooth voltage pulses between the two electrodes 96 and 97. According to FIG. 2, on the front of the apparatus there are provided two sockets 23, to which are connected the leads 91, 92 for ionization electrodes 94, 95. Sockets 24 are used for the connection of leads 92, 93 of faradization electrodes 96, 97. Below the sockets 23 is provided a recess i.e., calibration terminal, 25 used for the presetting of the ionization current. Prior at the start of treatment, the operator inserts into recess 25 a specific element having a resistance value corresponding to the tissue to be treated. Indicating instrument 30, as shown in FIG. 7, then indicates the current value set with potentiometer knob 21. The same applies to recess or calibration point 26 located beneath sockets 24. The operator inserts into the latter recess an element having a resistance value corresponding to the tissue to undergo faradization treatment. By means of potentiometer knob 22, the operator sets the desired voltage value, which is indicated by instrument 30. In certain cases, it is advantageous if the high frequency therapy is switched on and off at certain intervals and ionization treatment is continued via electrodes 94, 95 and/or faradization treatment is continued via electrodes 96, 97. Button 27 is used in such a case, being directly connected to control circuit 6. For example, through operating button 27 a specific, preprogrammed time rhythm of switching on and off the high frequency oscillator 7 can be brought about. For example, oscillator 7 can be switched on for 4 minutes and off for 2 minutes. To complete the description of FIG. 2, reference is made to switch 28 which switches on and off the complete apparatus and is operated by the operator.

Figure 3:
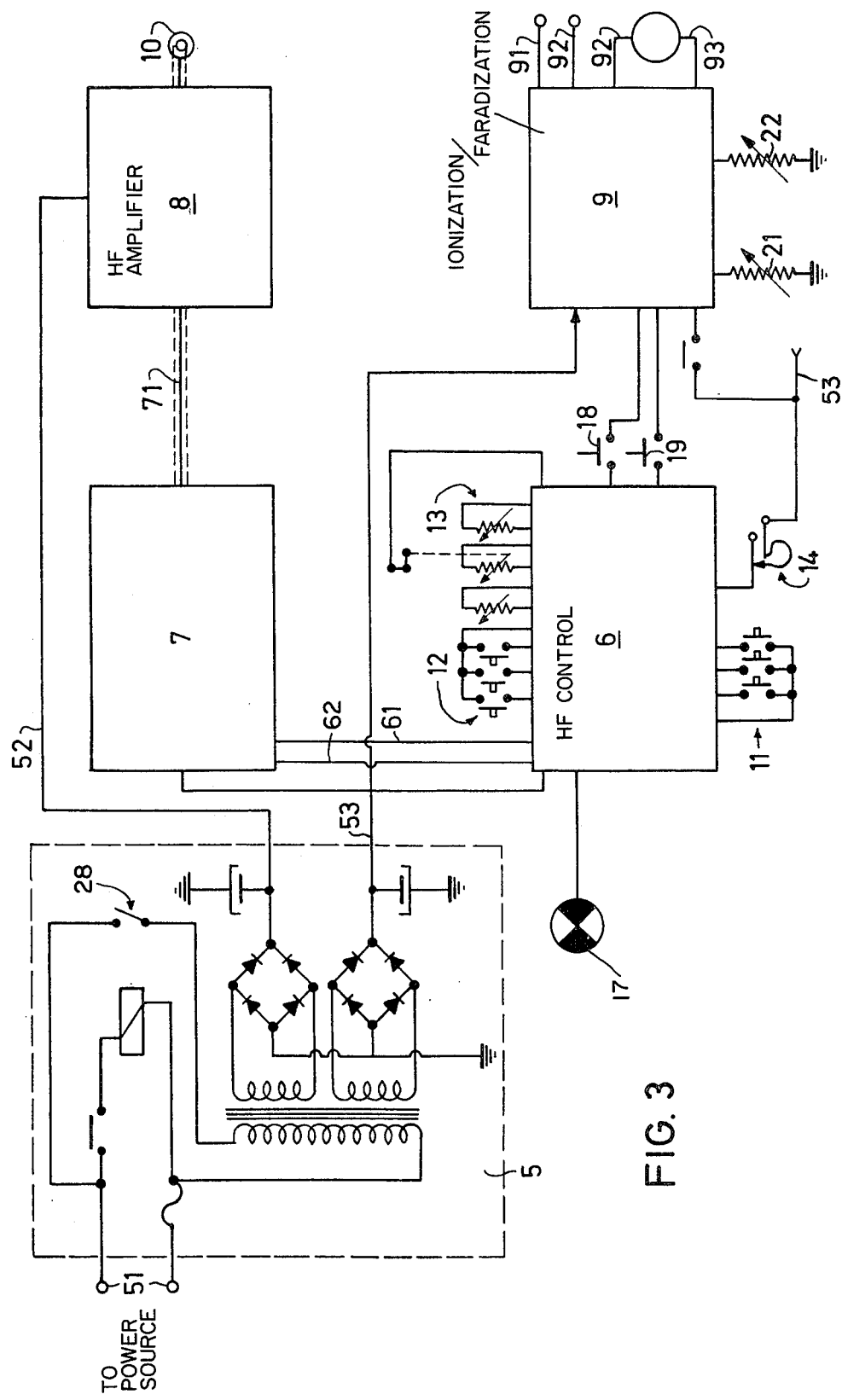
FIG. 3 a circuit diagram of the apparatus of FIG. 1 partly in block form.

FIG. 3 shows in detailed form the power supply means 5 which is connected to the normal electrical current source via terminals 51. This power supply means contains in known manner a fuse, switch, transformers with various taps for the two voltages and rectifier circuits, but no specific description will be provided thereof because they are known. The 60 volts, referred to in connection with FIG. 1, reaches the high frequency final amplifier 8 via lead 52. The d.c. voltage of 24 V passes via lead 53 to high frequency oscillator 7, circuit 9 and control circuit 6. FIG. 3 shows the buttons or switches 11 for setting the pulse energy, buttons or switches 12 for setting the pulse repetition frequency, and setting devices 13 constructed as variable resistors for the time duration of the pulses. The clock 14 for terminating treatment is also shown. The control signals for energy, pulse repetition frequency, and pulse duration are passed via multi-conductor cable 61 to high frequency oscillator 7. The scanned high frequency pulses pass via lead 71 to the high frequency final amplifier 8, in which they are amplified to approximately 300 volts and in this way reach the treatment head 10. By means of the indicated switches 18 and 19, control circuit 6 operates circuit 9. Circuit 9 is switched on by means of these switches for ionization (leads 91, 92) and/or for faradization (leads 92, 93). The two potentiometers 21, 22 set the current for the ionization and the voltage for faradization.

Figure 4:
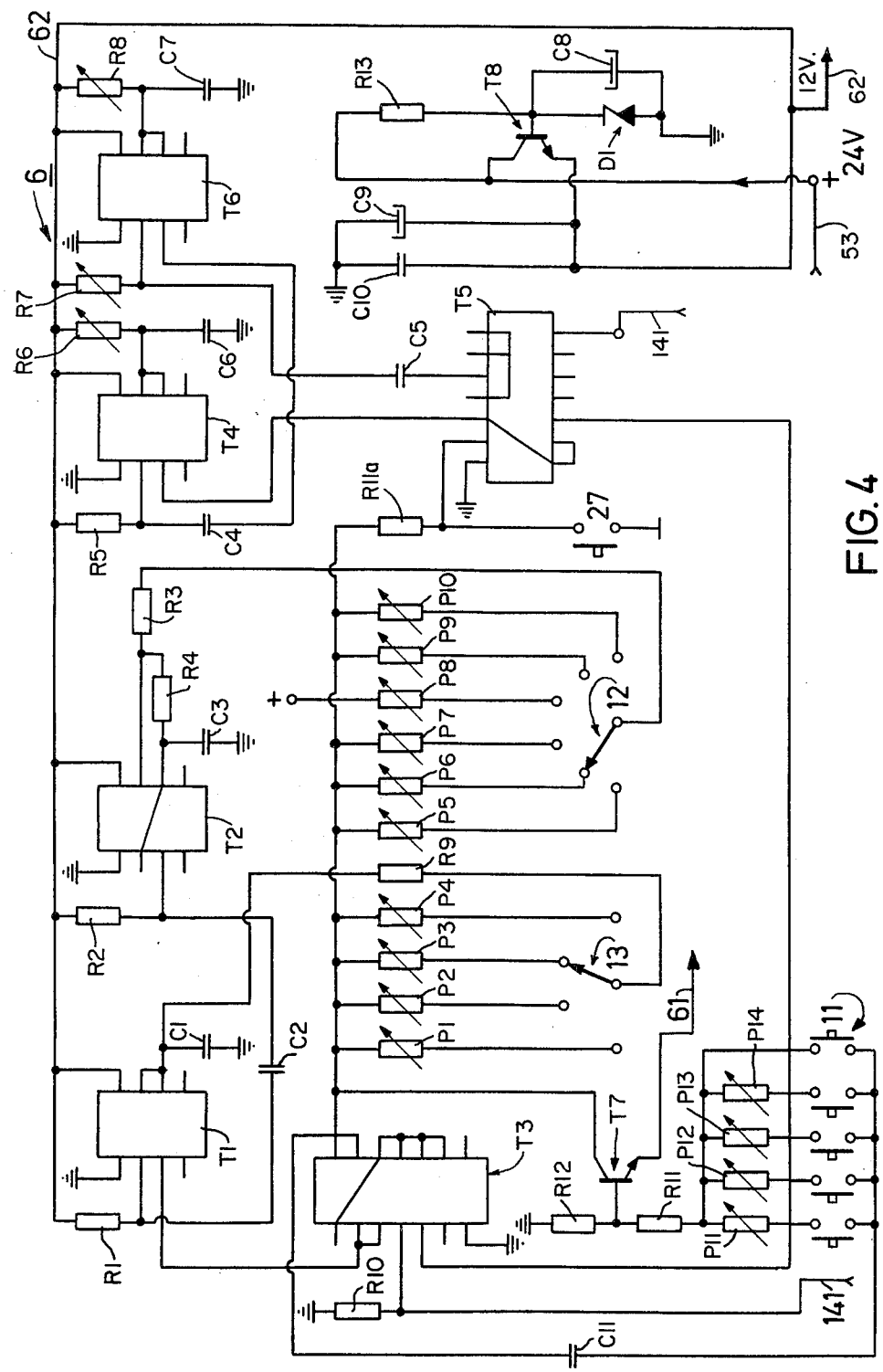
FIG. 4 a circuit diagram of the control circuit of the apparatus of FIG. 1.

FIG. 4 shows the control circuit 6 in detail. The desired amplitude of the output of the high frequency pulses is set by means of push buttons 11 which, by means of adjustable resistors, are connected to the base of a transistor T7. The buttons or switches 12 set the desired pulse repetition frequency by means of rheostats P5 to P10. The buttons or switches 13 set the desired time duration or length of each high frequency pulse by means of rheostats P1 to P4. When switches 11, 12 and 13 are set to the desired value, transistor T7 supplies the control pulses set by the switches to the preamplifier part in high frequency oscillator 7 by means of lead 61. Transistor T7 is controlled by the monostable oscillator T1 responsible for the pulse length and monostable oscillator T2 responsible for the pulse repetition frequency. The output signals of both monostable oscillators T1, T2 are supplied to the sweep circuit T3. Sweep circuit T3 only relays the output signals of the two monostable oscillators if by means of lead 141 clock 14 controls the sweep circuit. In this case, the output signals pass from sweep circuit T3 via coupling capacitors C11 and the operated button 11 to the particular one of resistors P11 - P14 and through R11 to the base of transistor T7. The control pulses are amplified by transistor T7 and pass via lead 61 to the preamplifier part of oscillator 7. The preamplifier part is described in greater detail in FIG. 5. FIG. 4 shows button 27. As has already been mentioned in connection with FIG. 2, button 27 is operated if during the joint application of ionization and/or faradization, high frequency therapy is to be used discontinuously, which means that e.g. high frequency therapy is switched on for 4 minutes and off for 2 minutes. This sequence of on/off cycles is repeated here, after depressing button 27 of FIG. 4. The requisite circuit comprises monostable oscillators T5, T4, T6 with the appropriate resistors and capacitors R5, R6, R7, R8, R11a, C4, C5, C6, C7. Integrated circuits such as conventional timers can be used for the monostable oscillators. Control circuit 6 of FIG. 4 is supplied by a constant voltage circuit of 12 V. The 24 V input voltage to the circuit including Zener diode D1, transistor T8, resistor R13, and capacitor C8 and at one output of capacitor C10 is supplied as a 12 V output to lead 62.

Figure 5:
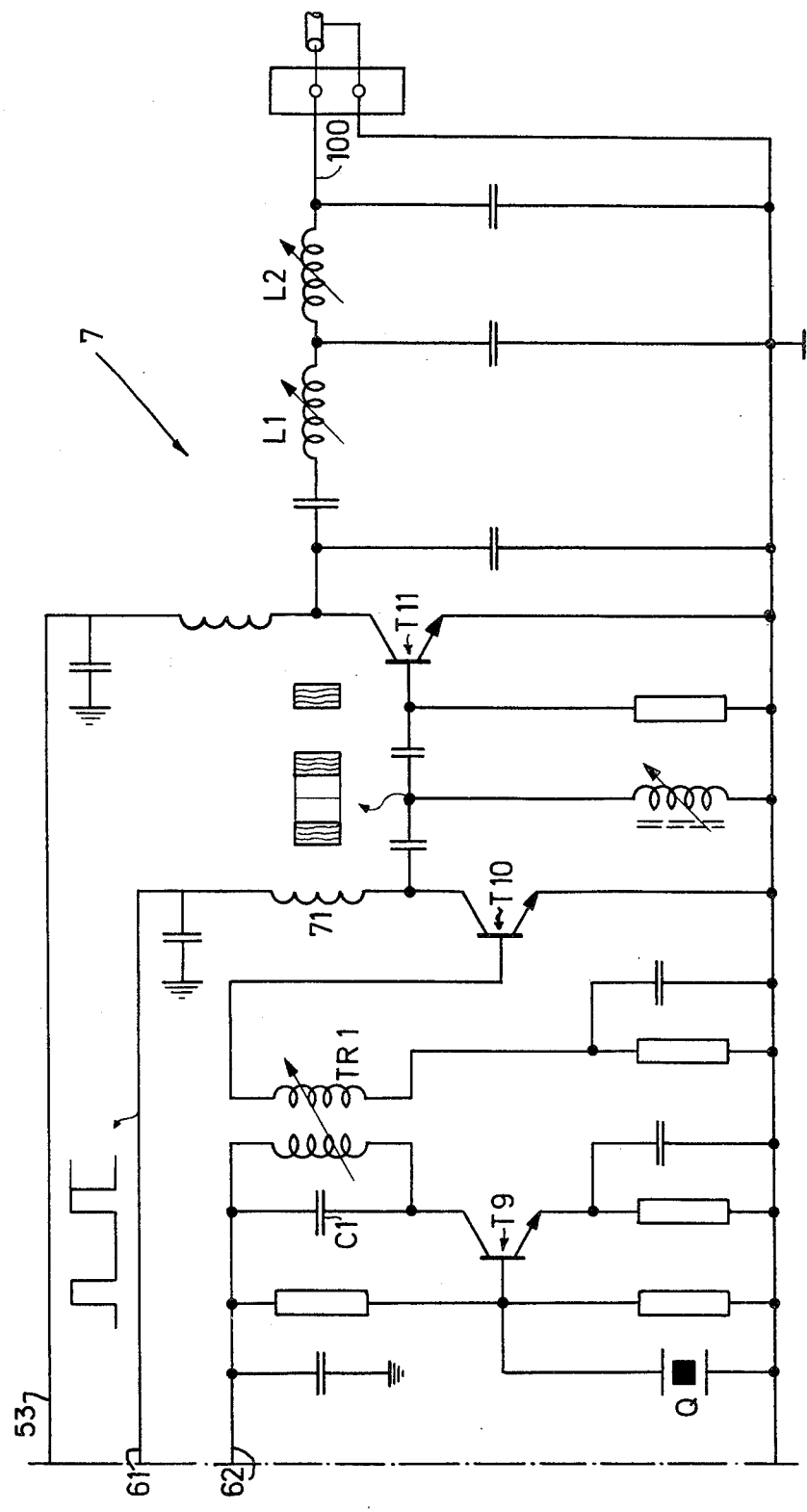
FIG. 5 a circuit diagram of a high frequency oscillator-preamplifier of the apparatus of FIG. 1.
Figure 6:
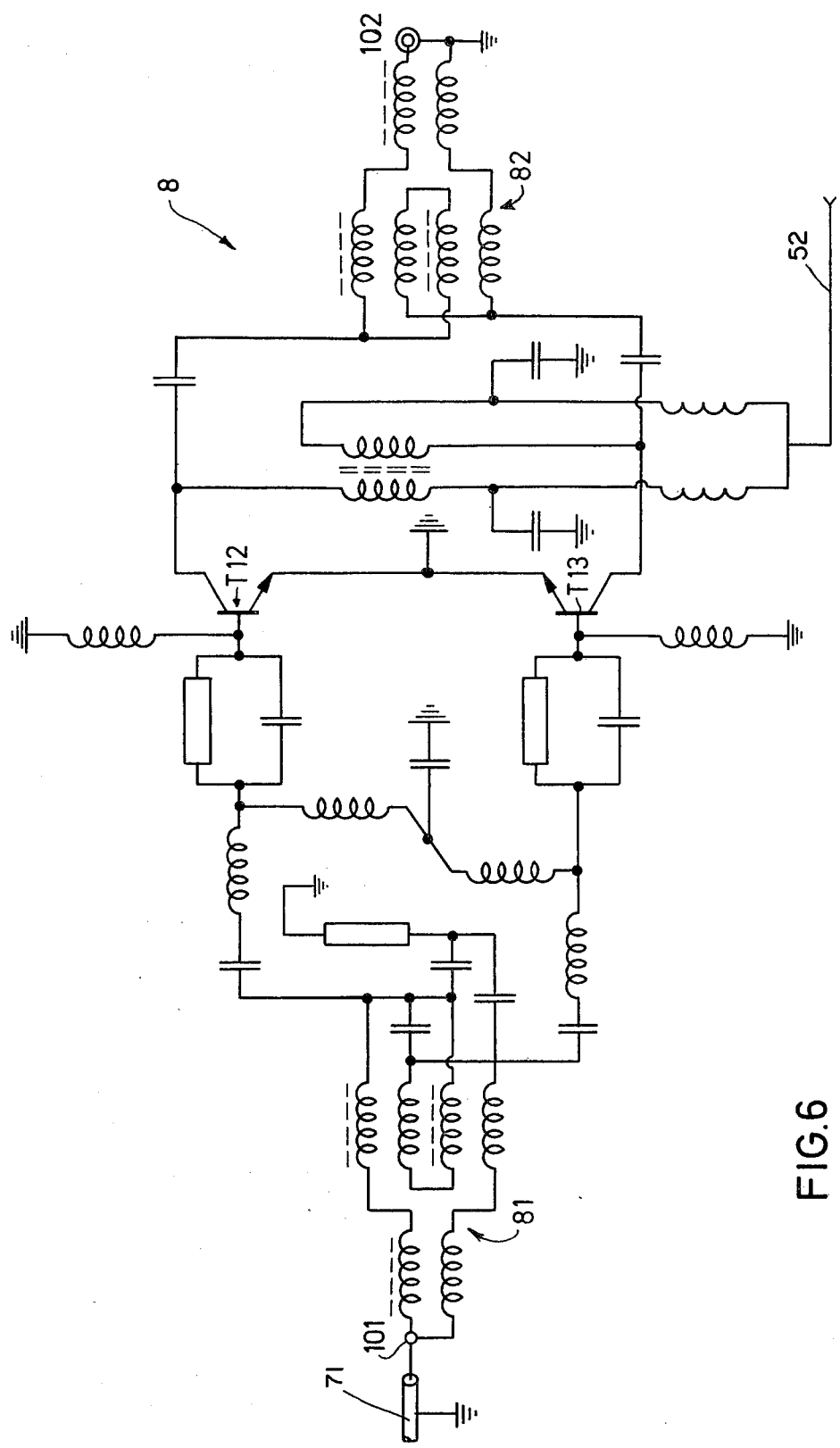
FIG. 6 a circuit diagram of a high frequency final amplifier of the apparatus of FIG. 1.

FIG. 5 shows the high frequency oscillator with the preamplifier. Lead 61 is used for supplying the control pulses of the amplitude, the repetition frequency and length set in control circuit 6. Lead 62 is used for the supply of regulated 12 volts from control circuit 6 to the high frequency oscillator 7. The actual oscillator part comprises transistor T9, which by means of quartz crystal Q oscillates with a constant frequency of 27.120 MHz. These oscillations pass via capacitor C1 and the primary winding of high frequency transformer TR1. The control pulses of lead 61 pass via high frequency choke 71 to the collector of a further transistor T10, whose base receives the pulses from the secondary winding of the high frequency transformer TR1. This transistor acts as a modulator of the high frequency pulses of frequency 27.120 MHz, so that the base of the following transistor T11 is controlled in the rhythm of the control pulses of lead 61. Coupling capacitors and a variable high frequency impedance are provided for the purposes of better transmission. Transistor 11, to whose collector is applied the 24 v d.c. voltage, acts as an amplifier for the high frequency pulses of the desired repetition frequency and length. The amplified 30 V pulses pass to lead 100 by menas of a T-network comprising variable inductors and capacitors. The function of the T-network is to adapt the high frequency pulses to the 50 Ohm output of oscillator 7. These pulses now reach input 101 of high frequency final amplifier 8 through cable 71 which, as shown in FIG. 6, comprises known circuit elements, such as an asymmetrical, symmetrical i.e. single input to push-pull output, impedance transformer 81, two transistors T12, T13 and a symmetrical, asymmetrical i.e., push-pull input to single output impedance transformer 82. The amplifier is dimensioned as a wide band amplifier for frequencies 13.560 and 27.120 MHz. It functions as a push-pull amplifier of class C, amplification being 13 db. The high frequency pulses appear with a peak voltage of 300 V at output 102 of amplifier 8. These pulses which have a HF peak power of 2 KW, reach the treatment head 10 for the high frequency therapy.

FIG. 7 shows the two parts of circuit 9 in detailed form, whereby they are responsible for the ionization treatment by means of electrodes 94 and 95 and for the faradization treatment by means of electrodes 96, 97. As already stated in connection with FIG. 2, the desired treatment method is selected by depressing the desired buttons or knobs 18, 19, 20, 181, 182. Hereinafter, it is assumed that ionization is desired, whereby button 18 is depressed. It is also assumed that ionization with a continuous d.c. voltage is desired, for which purpose button 181 is depressed. After setting the clock 14 (FIG. 2) to the desired treatment period, voltage via lead 141 is applied to the base of transistor T2 (FIG. 7). The transistor is operated in the conductive state, so that voltage is applied to both sockets 23 and to the latter are connected the leads 91, 92 (FIG. 1). Using potentiometer 21, the operator sets the desired current intensity, which can be read off indicating instrument 30. If for a particular treatment, an upper current value is not to be exceeded, the operator briefly closes the two sockets 23 by means of device 25 and prior to the start of the actual treatment sets the upper threshold value by means of potentiometer 21 and indicating instrument 30. It is assumed that ionization is to take place with pulsating d.c. voltage, for which purpose one of the so-called automatic buttons 181 and 182 is depressed. This means that the actual actuation of one button releases the other. On depressing button 182 and starting the treatment by means of clock 14, the integrated circuits 71 are controlled. These circuits 71 comprise mutually influencing time generators which e.g. deliver a timing cycle every five seconds. Thus, there reaches the output of circuit 71 a signal which so influences the base of transistor T2 at specific intervals that the transistor opens and closes with a pulse repetition frequency of approx. 0.5 to 10 Hz. During these intervals, a pulsating d.c.

voltage is applied to sockets 23 and/or electrodes 94, 95. It is now assumed that faradization is desired. For this purpose, button 19 is depressed, button 18 having been released after the previous treatment. The length of the saw-tooth pulses and the repetition frequency thereof are set by means of potentiometers 191, 192 in integrated circuits 72. By means of lead 74, the base of transistor T5 is controlled in such a way that it switches on and off in the desired manner. By means of lead 731, the integrated circuit 73, constructed as adjustable square-wave generators are controlled. These integrated circuits 73 function as so-called interval switches. Voltage is applied to the primary winding 741 of transformer 75 in the invterval of switches 73. If by means of lead 74 the integrated circuit 72 now open and close transistor T5, current now flows via primary winding 741 in the desired manner, i.e. with the desired pulse repetition frequency and length. These desired pulses having the desired shape are transmitted to the secondary winding 742 of transformer 75 and consequently reach sockets 24 in which are located the leads 92 and 93 for faradization electrodes 96, 97. By means of potentiometer 22 and a further scale on measuring instrument 30, the desired current intensity is set. In FIG. 7, a measuring instrument 30 is provided for both ionization and for faradization, but this does not mean that a separate measuring instrument is necessary for each treatment. If for the faradization treatment the operator sets an upper threshold value for the faradization voltage, sockets 24 are briefly closed by means of device 26 and the threshold value is set by means of potentiometer 22 and indicating instrument 30.

FIG. 8 shows the high frequency treatment head 10 (FIGS. 1 and 2), which comprises a hood 103 fixed to treatment arm 104. The treatment arm is positioned on the actual apparatus by means of various articulations in such a way that the treatment head 10 can be brought into any desired position relative to the tissue. Casing 103, which is e.g. made from aluminium sheeting, is constructed as a reflector. A cyclindrical cover 105 made from plastic material is fixed to the lower part of the casing and carries the actual antenna 12 on antenna plate 106 and which is fixed thereto by means of clamping bolts. The tuning capacitor 107 within reflector 103 serves to tune antenna 106. Tuning capacitor 107 can be tuned with the aid of set screw 115. At points 108, high frequency cable 102 is connected to a circular conductive coating 109 to which is also fixed one pole of the observation lamp 110. This lamp lights up as soon as antenna 106 is supplied by high frequency amplifier 8 (FIG. 1). One end 111 of tuning capacitor 107 is connected to a conductive coating 112 (FIG. 10), which is located on the other side of the antenna 106 constructed as an insulating plate. The other connection 113 of capacitor 107 is connected to the other end of conductive coating 112. Capacitor 107 is connected by means of three bolts 114 to the antenna plate 106. These bolts 114 are not connected to either of the conductive coatings 109 or 112.

FIG. 9 shows the upper side of antenna plate 106 with the circular coating 109 of conductive material. Coating 109 is constructed as a resonant circuit coil. At the two points 115, high frequency cable 102 is fixed to said resonant circuit coil 109 which, although shown in circular form in FIG. 8, can also be elliptical.

FIG. 10 shows the other side of antenna plate 106 with a further conductive material 112. This conductive material 112 is in the present embodiment constructed as a so-called Archimedean spiral. The leads 111, 113 of tuning capacitor 107 are fixed to the two ends of the Archimedean spiral 112. The capacitive coupling between the two coatings 109 and 112 is particularly advantageous with the two embodiments of FIGS. 9 and 10. Antenna plate 106 is constructed as a plate or disk of insulating materials such as e.g. Pertinax brand or other rigid electrically insulating material coated with copper on both sides. It is finally pivoted out that for the optimization of the radiation of antenna 106 in treatment head 10, tuning by means of capacitor 107 and trimming device 108 is performed by locating a tool inserted through the access opening in the end of the cover to rotate near cylindrical cover 105 in FIG. 8 a bulb, not shown, connected to a coil, not shown, of e.g. 2½ turns of insulated 1.5 mm thick copper wire and suited for a voltage of e.g. 220 V and an output of 40 W. The diameter of this copper wire coil is approximately 130 mm. Optimum tuning is obtained if the bulb lights up very brightly.

The treatment head shown on FIGS. 8, 9 and 10 has a diameter of approximately 17 cm and a height of approximately 10 cm.

The other end of arm 104 of the treatment head shown in FIG. 10 is connected to the treatment apparatus. The connection point between arm 104 and the apparatus is constructed in such a way that the arm can be rotated by 360° in all possible directions and the power supply via high frequency cable 102 is not interrupted. The coupling essentially comprises a high frequency plug which is fitted into a corresponding high frequency socket. As a result, the treatment head with arm 104 can be separated easily and effortlessly from the actual apparatus when treatment is at an end. The treatment apparatus and treatment head can easily be transported by one person.

I claim:

1. An apparatus for maintaining the negative potential of human, animal and vegetable cells and/or for the penetration of substances into the cells, comprising a generator and control circuit means for producing high frequency pulses of adjustable repetition frequency, amplitude and duration and a d.c. circuit for selectively producing a d.c. voltage and a pulsating d.c. voltage for the ionization and d.c. pulses of predetermined shape and variable repetition frequency for the faradization of the tissue to be treated; means connected to the outputs of said generator and d.c. circuit for selectively applying said high frequency pulses, said ionization voltage and said faradization pulses produced thereby to the body; indicator means for indicating the magnitude of signals supplied to said means for applying; connector means in circuit relationship with the outputs of said generator and d.c. circuits for selectively connecting the generator and d.c. circuit outputs to calibration circuit elements having a load characteristic similar to that of the cells to be treated; and means for adjusting the level of signals produced and displayed on said indicator means while said elements are connected, whereby desired signal levels can be established before application thereof to the cells.

2. An apparatus according to claim 1, comprising a treatment head having a disk-like insulating plate which is coated on both sides for transmitting the high frequency pulses to the tissue.

3. An apparatus according to claim 2, wherein the insulating plate has on one side an annular, electrically conductive metal coating and on its other side a spiral, electrically conductive coating.

* * * * *